(12) United States Patent
Le et al.

(10) Patent No.: US 9,855,188 B2
(45) Date of Patent: Jan. 2, 2018

(54) SYSTEM AND METHOD FOR MULTIFUNCTIONAL MAGNETIC COUPLING JET

(71) Applicant: Luraco Technologies, Inc., Arlington, TX (US)

(72) Inventors: Kevin Le, Richland Hills, TX (US); Thanh Le, Grand Prairie, TX (US)

(73) Assignee: Luraco Technologies, Inc., Arlington, TX (US)

( * ) Notice: Subject to any disclaimer, the term of this patent is extended or adjusted under 35 U.S.C. 154(b) by 245 days.

(21) Appl. No.: 14/664,416

(22) Filed: Mar. 20, 2015

(65) Prior Publication Data

US 2015/0190308 A1 Jul. 9, 2015

Related U.S. Application Data

(62) Division of application No. 13/156,239, filed on Jun. 8, 2011, now abandoned.

(51) Int. Cl.

| | |
|---|---|
| *A61H 33/04* | (2006.01) |
| *A61H 33/00* | (2006.01) |
| *A61H 33/02* | (2006.01) |
| *H05B 33/08* | (2006.01) |
| *A61N 5/06* | (2006.01) |

(52) U.S. Cl.
CPC ....... *A61H 33/6047* (2013.01); *A61H 33/027* (2013.01); *A61H 33/6063* (2013.01); *H05B 33/086* (2013.01); *A61H 2033/0054* (2013.01); *A61H 2033/0083* (2013.01); *A61H 2201/0176* (2013.01); *A61H 2201/1207* (2013.01); *A61H 2201/1215* (2013.01); *A61N 2005/0652* (2013.01); *A61N 2005/0663* (2013.01); *A61N 2005/0668* (2013.01)

(58) Field of Classification Search
USPC .............................................. 4/541.6, 541.3
See application file for complete search history.

(56) References Cited

U.S. PATENT DOCUMENTS

| | | |
|---|---|---|
| 2,506,886 A | 5/1950 | Okulitch et al. |
| 2,951,689 A | 9/1960 | Asp et al. |
| 2,958,517 A | 11/1960 | Harker et al. |
| 3,299,819 A | 1/1967 | McCoy |

(Continued)

FOREIGN PATENT DOCUMENTS

GB 2156218 A 10/1985

*Primary Examiner* — Lauren Crane
(74) *Attorney, Agent, or Firm* — Haynes and Boone, LLP

(57) ABSTRACT

An apparatus including a motor assembly having a motor. A jet assembly coupled to the motor assembly having an inlet and outlet aperture. An impeller configured to rotate causing a first fluid to flow into the inlet aperture and out the outlet aperture. A fluid guider that includes at least one wall member defining a first channel configured to guide the first fluid from the inlet aperture into the cavity. Additionally, the fluid guider includes at least one post defining a second channel extending through the post. The second channel configured to guide the first fluid from the cavity towards the outlet aperture and output the first fluid at an oblique angle with respect to a longitudinal axis of the post. A second fluid channel member configured to provide a second fluid out the outlet aperture. A light source configured to illuminate the first fluid.

22 Claims, 10 Drawing Sheets

(56) References Cited

U.S. PATENT DOCUMENTS

| | | |
|---|---|---|
| 3,572,651 A | 3/1971 | Harker |
| 3,932,068 A | 1/1976 | Zimmermann |
| 3,941,517 A | 3/1976 | Miyahara |
| 4,115,040 A | 9/1978 | Knorr |
| 4,135,863 A | 1/1979 | Davis et al. |
| 4,304,532 A | 12/1981 | McCoy |
| 4,513,773 A | 4/1985 | Friedson et al. |
| 4,523,580 A | 6/1985 | Tureaud |
| 4,569,337 A | 2/1986 | Baumann et al. |
| 4,606,698 A | 8/1986 | Clausen et al. |
| 5,414,878 A | 5/1995 | Booth |
| 5,548,854 A * | 8/1996 | Bloemer ................ A61H 23/04 4/541.6 |
| 5,587,023 A | 12/1996 | Booth |
| 7,108,202 B1 | 9/2006 | Chang |
| 7,111,334 B2 | 9/2006 | Chen |
| 7,168,107 B2 | 1/2007 | Gruenwald |
| 7,393,188 B2 | 7/2008 | Lawyer et al. |
| 8,680,699 B2 | 3/2014 | Tran et al. |
| RE45,844 E | 1/2016 | Long |
| 2005/0120473 A1* | 6/2005 | Southon ............. A61H 33/6063 4/541.6 |
| 2007/0136943 A1 | 6/2007 | Long |
| 2009/0276952 A1 | 11/2009 | Wooten |
| 2010/0239435 A1 | 9/2010 | Le et al. |
| 2011/0004994 A1 | 1/2011 | Le et al. |
| 2012/0311777 A1 | 12/2012 | Le et al. |

* cited by examiner

SYSTEM AND METHOD FOR MULTIFUNCTIONAL MAGNETIC COUPLING JET

The present application is a divisional application of U.S. patent application Ser. No. 13/156,239, filed Jun. 8, 2011, which is incorporated herein by reference in its entirety.

BACKGROUND

Spa devices are used in commercial and recreational settings for hydrotherapy, massage, stimulation, pedicure, and bathing purposes. Typical spa devices include a motor that drives a pump to circulate water from the spa device. In particular, a shaft of the motor is used to directly mount an impeller which is then used to circulate water into and out of the spa device. Since the motor may not operate wet, a seal or a series of seals may be required to prevent water from entering the motor. The seals will wear to the point where water will enter the motor and consequently, the entering water may cause the motor to burn out. At this point, the motor assembly may be replaced in order to continue operation. This is expensive and may take several hours in which to perform.

Additionally, because typical spa devices have extensive piping systems that are built into the spa device to transporter water, the spa devices are traditionally difficult to clean. This results in downtime and complicated maintenance schedules to clean such spa devices. Furthermore, if a spa device has a light source associated with it, to replace or repair such a light source can be time consuming and complicated when the light source is not easily accessible.

The subject matter of the present disclosure overcomes one or more of the shortcomings of the above described spa devices.

SUMMARY

In one exemplary aspect, the present disclosure is directed to an apparatus. The apparatus includes a motor assembly having a motor and a magnetic array such that the motor is configured to drive the magnetic array. The apparatus also includes a jet assembly coupled to the motor assembly. The jet assembly includes an inlet aperture configured to receive a first fluid. Additionally, the jet assembly includes an outlet aperture surrounded by the inlet aperture and centrally disposed about the jet assembly. The outlet aperture configured to output the first fluid. The jet assembly further includes an impeller positioned within a cavity of the jet assembly and configured to rotate within the cavity when the magnetic array is driven such that rotation of the impeller causes the first fluid to flow into the inlet aperture and out the outlet aperture. Also, the jet assembly has a fluid guider in communication with the inlet and outlet apertures. The fluid guider includes at least one wall member defining a first channel configured to guide the first fluid from the inlet aperture into the cavity. Additionally, the fluid guider includes at least one post defining a second channel extending through the post. The second channel configured to guide the first fluid from the cavity towards the outlet aperture and output the first fluid at an oblique angle with respect to a longitudinal axis of the post. Furthermore, the jet assembly includes a second fluid channel member disposed within the outlet aperture and configured to provide a second fluid out the outlet aperture. Moreover, the jet assembly includes a light source configured to emit a light that illuminates the first fluid when the magnetic array is driven.

In one exemplary aspect, the present disclosure is directed to a method for distributing fluids using a magnetically coupled jet assembly and motor assembly. The method includes receiving a first fluid through an inlet aperture of a jet assembly. Also, the method includes guiding the first fluid into a cavity of the jet assembly through a pathway defined by a wall member of a fluid guider. Furthermore, the method includes driving the motor assembly to rotate a magnetic array thereby rotating an impeller within the cavity of the jet assembly. Additionally, the method includes pressurizing the first fluid within the cavity by rotation of the impeller. Moreover, the method includes guiding the pressurized first fluid into a first channel of a first post of the fluid guider to form a first pressurized fluid stream, the first post extending along a longitudinal axis. The method further includes guiding the first pressurized fluid stream toward a second fluid channel member at a first oblique angle with respect to the longitudinal axis. The second fluid channel member disposed within an outlet aperture of the jet assembly and containing a second fluid. The method also includes combining the first pressurized fluid stream with the second fluid to form a jet fluid stream. Finally, the method includes outputting the jet fluid stream through the outlet aperture.

In one exemplary aspect, the present disclosure is directed to a system. The system includes a motor assembly having a motor and a magnetic array such that the motor is configured to drive the magnetic array. Also, the system has a jet assembly magnetically coupled to the motor assembly. The jet assembly includes an inlet aperture configured to receive a first fluid. Additionally, the jet assembly has an outlet aperture surrounded by the inlet aperture and centrally disposed about the jet assembly. The outlet aperture configured to output the first fluid. The jet assembly further includes an impeller positioned within a cavity of the jet assembly and configured to rotate within the cavity when the magnetic array is driven such that rotation of the impeller causes the first fluid to flow into the inlet aperture and out the outlet aperture. Furthermore, the jet assembly includes a fluid guider in communication with the inlet and outlet apertures. The fluid guider includes at least one wall member defining a first channel configured to guide the first fluid from the inlet aperture into the cavity. Also, the fluid guider includes at least one post defining a second channel extending through the post. The second channel configured to guide the first fluid from the cavity towards the outlet aperture and output the first fluid at an oblique angle with respect to a longitudinal axis of the post. Additionally, the jet assembly includes a second fluid channel member disposed within the outlet aperture and configured to provide a second fluid out the outlet aperture. Moreover, the jet assembly includes a light source configured to emit a light that illuminates the first fluid when the magnetic array is driven. The system further includes a fluid container having an interior portion for containing the first fluid. The interior portion having a first recess formed therein sized and shape to receive the motor assembly and the jet assembly. Also, the system includes a system controller coupled to and operable to control the motor assembly and the jet assembly.

BRIEF DESCRIPTION OF THE DRAWINGS

Aspects of the present disclosure are best understood from the following detailed description when read with the accompanying figures.

DETAILED DESCRIPTION

Figure 1:
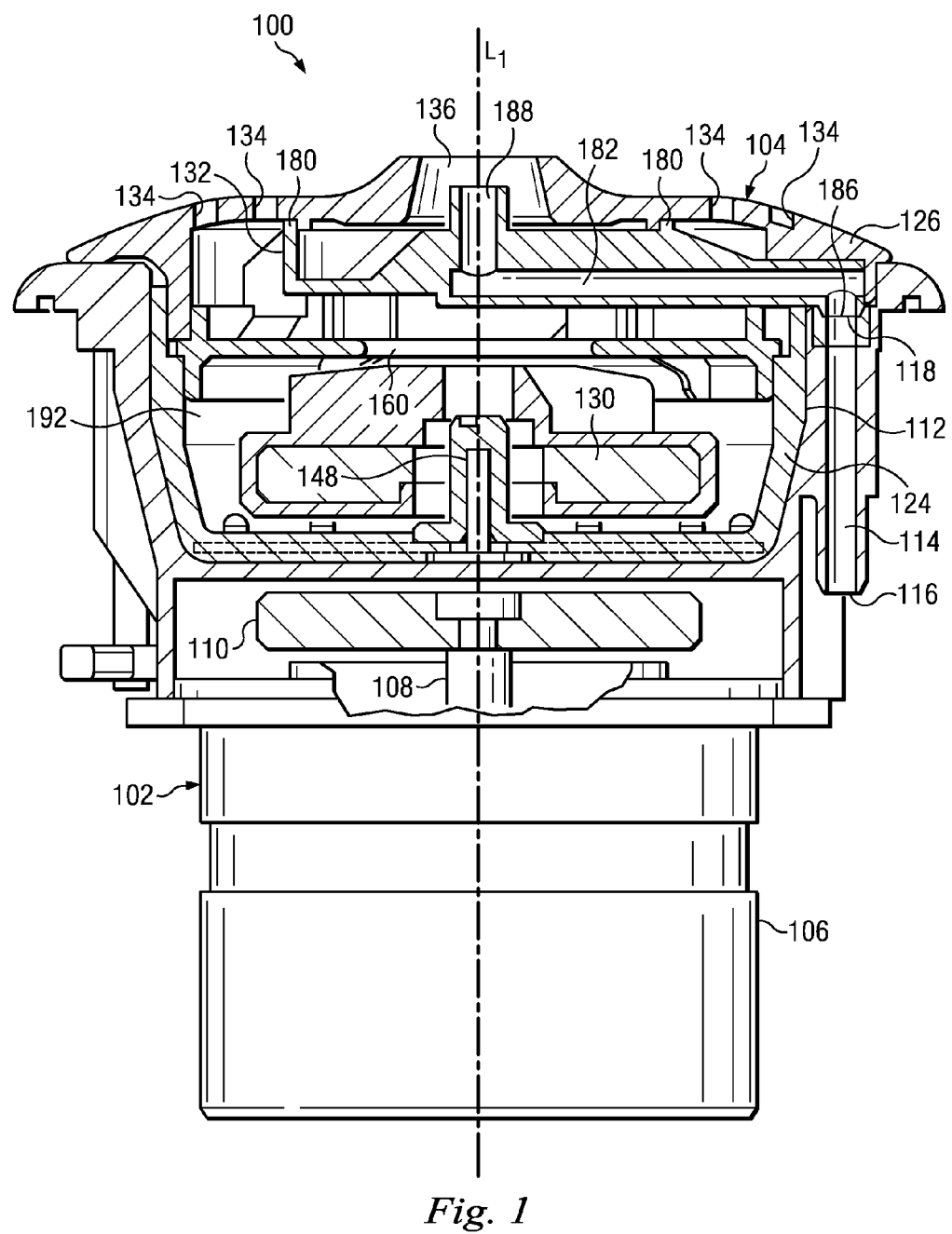
FIG. 1 illustrates a cross-sectional view of an embodiment of a pump according to various aspects of the present disclosure.
Figure 2:
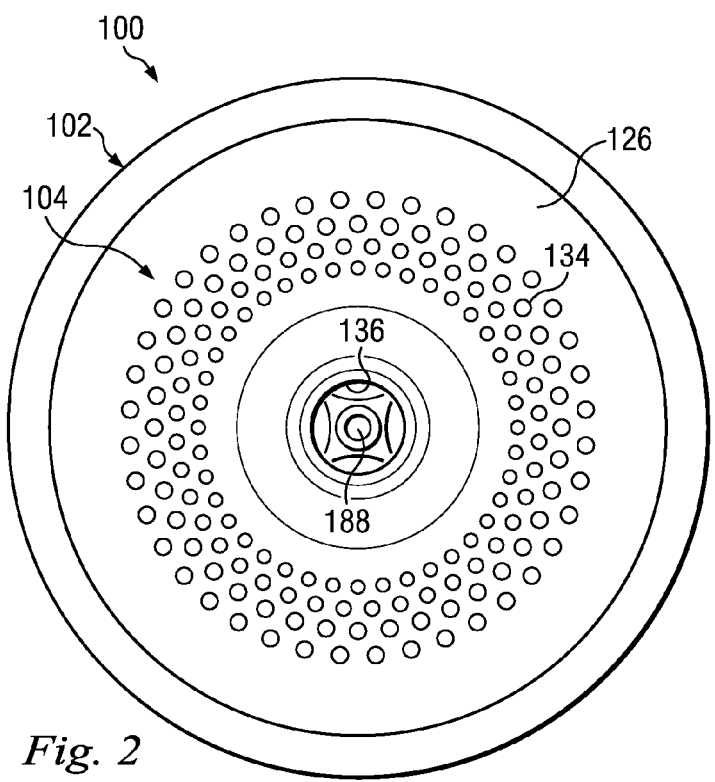
FIG. 2 illustrates a front view of the pump of FIG. 1 of the present invention.
Figure 3:
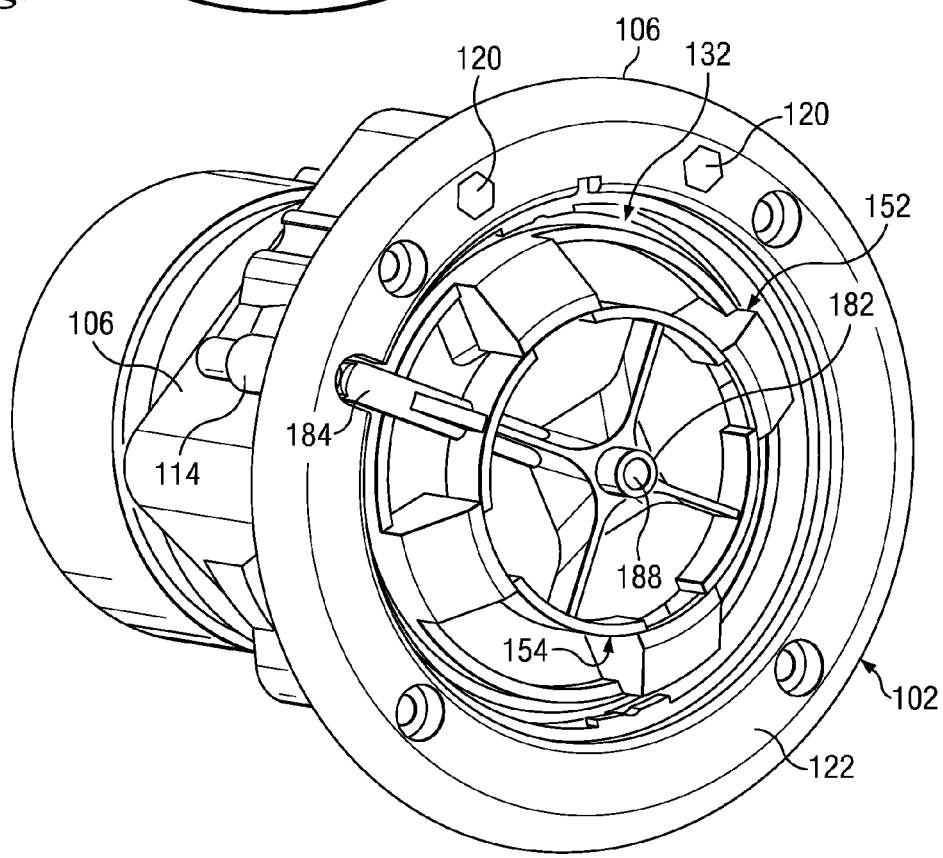
FIG. 3 illustrates a perspective front view of the pump of FIG. 1 with the front cover removed for clarity purposes.

FIGS. 1-3 show a pump 100 that can be used in fluid applications such as hydrotherapy, massage, stimulation, pedicure, bathing purposes, and the like to circulate and propel fluids therefrom. FIG. 1 illustrates a cross-sectional view of pump 100. FIG. 2 illustrates a front view of the pump 100. FIG. 3 illustrates a perspective front view of the pump 100 without a front cover to provide additional details. As described in more detail below, pump 100 extends along longitudinal axis $L_1$ and includes a motor assembly 102 that is magnetically coupled to a multifunctional jet assembly 104.

The motor assembly 102 includes a housing 106 that encloses some or all of the components of motor assembly 102. As shown within housing 106, motor assembly 102 includes a shaft member 108 that is coupled to a magnetic pole array 110. Magnetic pole array 110 is formed of magnetic material and is magnetized. Thus, magnetic pole array 110 generates a magnetic field.

In that regard, motor assembly 102 may include and/or be coupled to a power source that enables rotation of the shaft member 108. Upon operation of motor assembly 102, shaft member 108 is rotated such that the magnetic field generated by magnetic pole array 110 moves or fluctuates in accordance with the rotation of the magnetic pole array 110.

Figure 4:
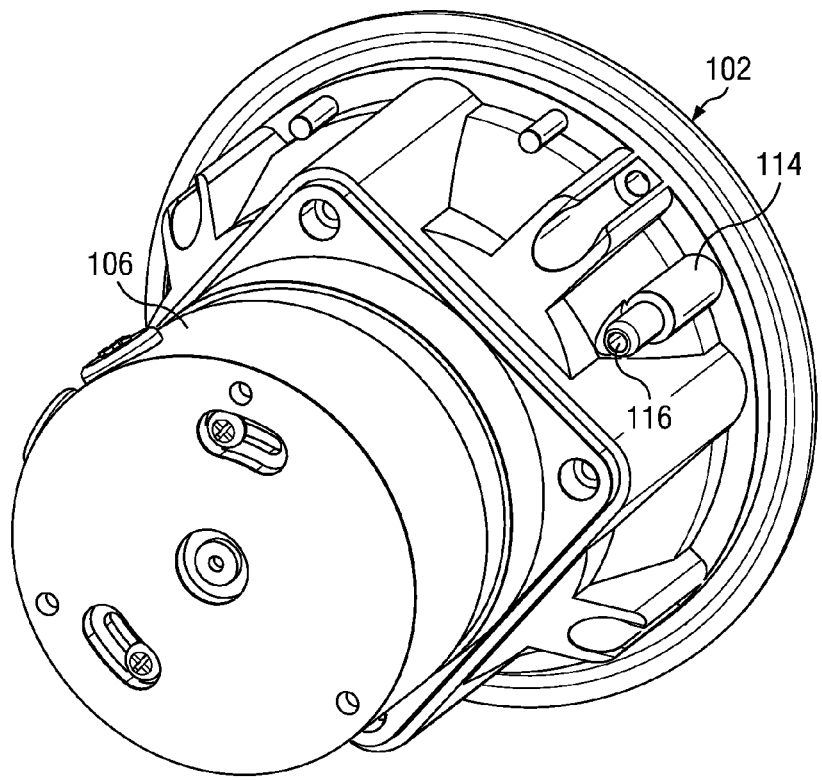
FIG. 4 illustrates a perspective rear view of the motor assembly of the pump of FIG. 1.
Figure 5:
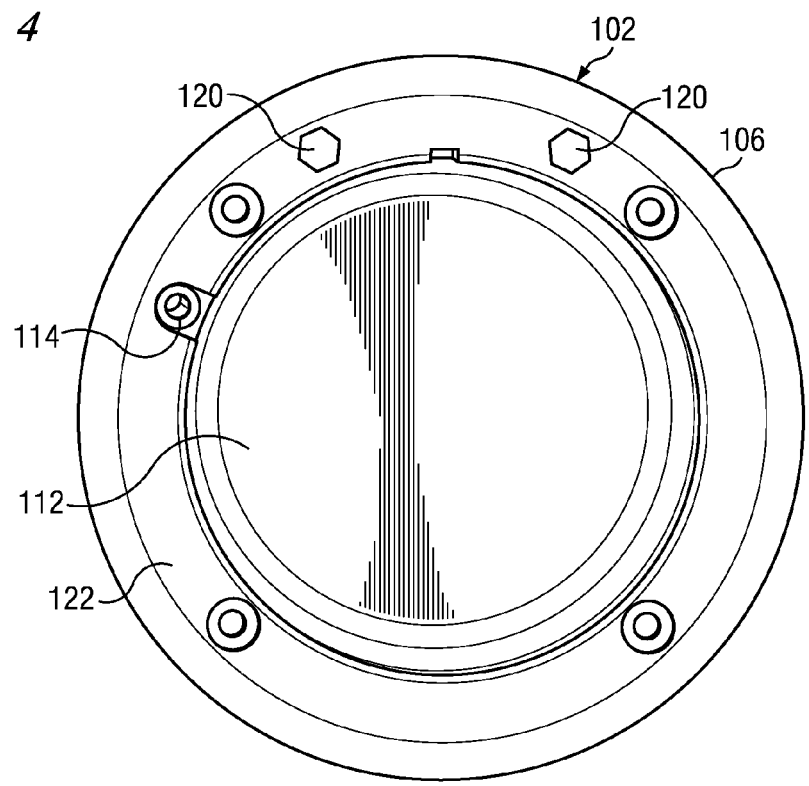
FIG. 5 illustrates a front view of the motor assembly of FIG. 4.

FIGS. 4 and 5 show additional views of motor assembly 102. In particular, FIG. 5 demonstrates that motor assembly 102 has a recess 112 sized and shaped for receiving jet assembly 104. As shown in FIG. 1, when pump 100 is assembled jet assembly 104 is positioned within recess 112 of motor assembly 102. As will described in greater detail below, jet assembly 104 is magnetically coupled to motor assembly 102 when jet assembly 104 is positioned within recess 112.

Furthermore, motor assembly 102 includes an air channel 114, or air channel member. In that regard, air channel 114 includes an inlet 116 and outlet 118. As will be described in greater detail below, air channel 114, in part, enables the jet assembly 104 to produce a jet stream of fluid that includes an air mixture.

Additionally, as best shown in FIGS. 3 and 5, the motor assembly 102 includes sensors 120. As shown, sensors 120 are positioned on a front facing surface 122, or annular flange, of housing 106. Sensors 120 include electrodes that act as level sensors that sense the level of fluid around the pump 100. If sensors 120 detect that the level of fluid around pump 100 is below a predetermined level or value, then the sensors can shut off pump 100. For example, if pump 100 is being used in a spa application, sensors 120 can detect the level of fluid in a basin in which the pump 100 is being used. If the fluid level is too low such that continued operation of pump 100 may cause damage to the pump, then sensors 120 send a signal to motor assembly 102 to stop the motor assembly from operating. Therefore, sensors 120 act as a safety mechanism that prevents the pump 100 from burning out if fluid levels are too low for proper functioning of pump 100.

Although sensors 120 have been described as being associated with particular aspects of motor assembly 102, it is contemplated that sensors 120 can be associated with other and/or additional portions of motor assembly 102. Additionally, in other embodiments sensors 120 can be associated with jet assembly 104. Furthermore, in other embodiments sensors 120 can be associated with both motor assembly 102 and jet assembly 104. Moreover, although two sensors 120 are shown it is contemplated that one sensor or more than two sensors can be used to detect fluid levels around pump 100.

Figure 6:
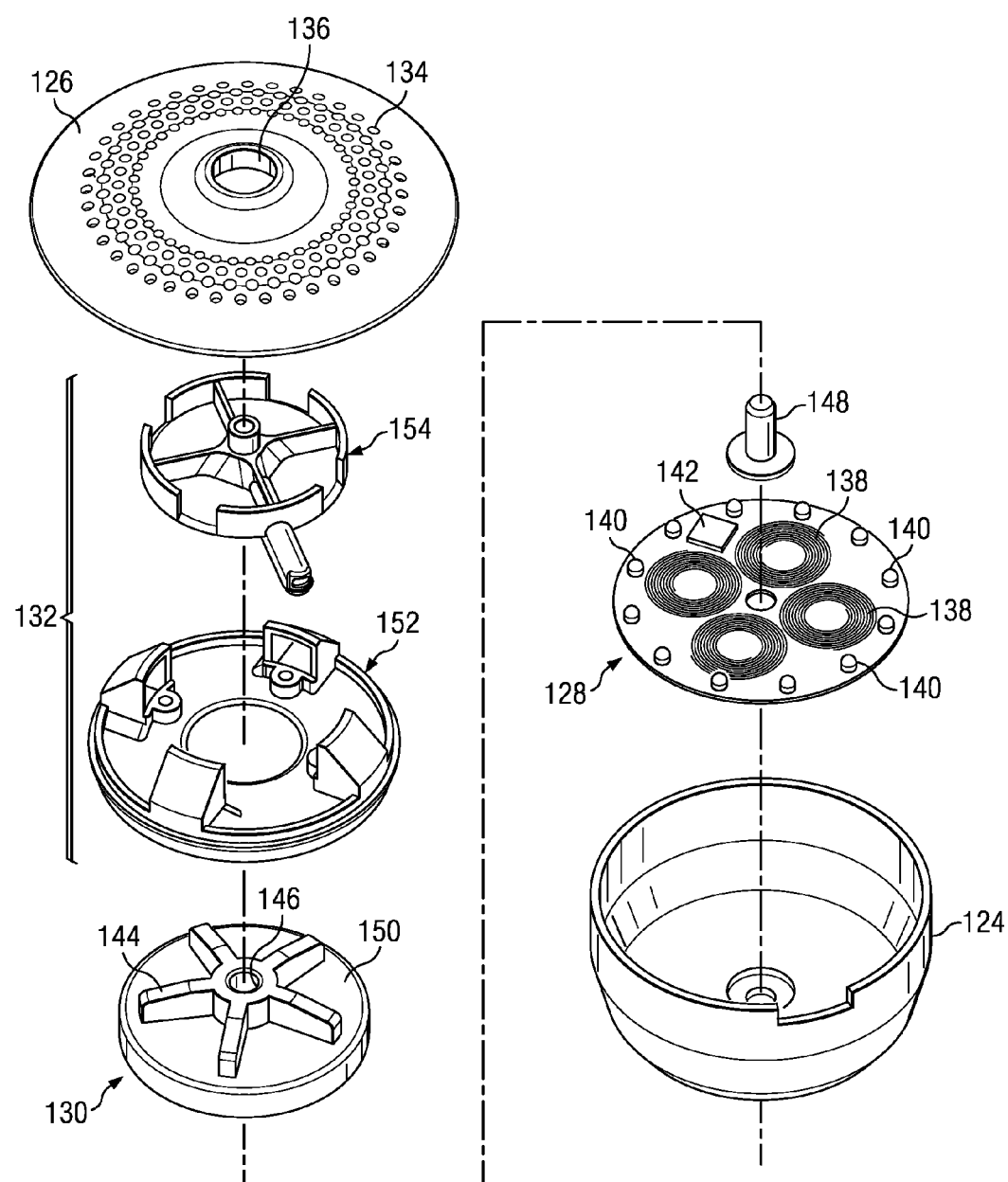
FIG. 6 illustrates an exploded perspective view of a jet assembly of the pump of FIG. 1.

FIG. 6 illustrates an exploded perspective view of jet assembly 104 of the pump 100. As shown in FIGS. 1 and 6, jet assembly 104 includes a back cover 124 and front cover 126. Housed between back cover 124 and front cover 126 is an energy harvesting component 128, an impeller 130, and a fluid guider 132.

As shown in FIG. 1, back cover 124 and front cover 126 are coupled together when jet assembly 104 is fully assembled. Back cover 124 has a profile that substantially matches the profile of recess 112 of motor assembly 102 as shown in FIG. 1. Additionally, referencing FIG. 2, front cover 126 has an array of inlet apertures 134.

Inlet apertures 134 form a circular pattern around the front cover 126. Here, the array of inlet apertures 134 includes four circular patterns. As shown, each inlet aperture within each circular pattern has substantially the same inlet size. Moreover, each respective circular pattern is formed of inlet apertures having a different size than the inlet apertures in adjacent circular pattern. In that regard, the respective size of the inlet apertures 134 within each respective circular pattern increases in size from the central portion of front cover 126 toward the outer edge of front cover 126. As such, the circular pattern of inlet apertures 134 positioned closest to the central portion of front cover 126 have the smallest apertures while the circular pattern of inlet apertures 134 positioned furthest from the central portion of front cover 126 have the largest apertures. In other words, a gradual gradient change for fluid intake in jet assembly 104 is formed across inlet apertures 134.

In other embodiments the number of circular patterns may be less than or greater than the four patterns shown in FIG. 2. Furthermore, in other embodiments each inlet aperture 134 can have substantially the same size or each inlet aperture 134 can be of different sizes. Moreover, in other embodiments the arrangement and/or sizing of inlet apertures 134 can vary between adjacent apertures and adjacent circular patterns.

Outlet aperture 136 is centrally positioned on front cover 136. Inlet apertures 134 surround outlet aperture 136. As shown, the circular pattern of inlet apertures 134 and outlet aperture 136 form substantially concentric circles. Thus, because inlet apertures 134 surround outlet apertures 136, inlet apertures 134 are positioned closer to the outer edge of front cover 126 than is the outlet aperture 136. As will be discussed in greater detail below, inlet apertures 134 are configured to receive fluids into the jet assembly 104 while outlet aperture 136 is configured to allow a jet stream of fluid to be expelled, outputted, and/or propelled from jet assembly 104.

Referring to FIG. 6, as discussed above, jet assembly 104 includes energy harvester component 128. Energy harvester component 128 is configured to garner and utilize the magnetic waves produced from the rotation of magnetic pole array 110 through electromagnetic induction. In that regard, energy harvester 128 includes coils 138 designed to capture the magnetic waves to provide energy to a light source or light emitting diode (LED) array 140. As shown, LED array 140 forms a circular pattern along the edge of energy harvesting component 128. LED array 140 can be comprised of all the same type of LEDs having the same color. Additionally, LED array 140 can be comprised of LEDs where each LED has a different color. Furthermore, LED array 140 can be comprised of a mixture of LEDs where at least two or more have the same color and a least another LED has a different color.

Moreover, it is contemplated that each LED within LED array 140 can be any visible color or non-visible colors of light know to be capable of being produced by LEDs. Additionally, it is contemplated that each LED can illuminate as one or more visible or non-visible colors of light at the same time.

Coils 138 and LED array 140 are coupled to controller 142. Controller 142 controls various parameters associated with LED array 140 as well as the harvesting of energy from coils 138. Controller 142 is configured to control each individual LED within array 140 individually. For example, controller 142 controls the intensity of each of the LEDs in LED array 140. In that regard, controller 140 can cause each LED within LED array 140 to illuminate at the same intensity or at a varying intensity with respect to other LEDs in the array. Additionally, controller 142 controls the sequence and/or pattern of illumination exhibited by LED array 140. For example, controller 142 can cause the LEDs to illuminate sequentially, in unison, or any random pattern alone or in combination with other LEDs in LED array 140. Moreover, controller 142 can control LED array 140 such that a specified color and/or colors are exhibited by LED array 140. For example, LED array 140 may illuminate as a single uniform color or as multiple colors being producing by different LEDs.

Here, energy harvester component 128 is formed on a printed circuit board. However, in other embodiments it is contemplated that energy harvester component 128 is integrated into other components of jet assembly 104. For example, the components of energy harvester 128, such a coils 138, LED array 140, and controller 142 are integrated into back cover 124 of jet assembly 104.

Referring to FIGS. 1 and 6, jet assembly 104 includes impeller 130. The impeller 130 includes a circular array of arm members 144 and an opening 146 that receives a shaft member 148 of jet assembly 104. Impeller 130 is configured to rotate about shaft member 148. Impeller 130 is formed in whole or in part of a magnetic pole array 150 that, as discussed below, interacts with magnetic pole array 110 of motor assembly 102 to rotate impeller 130 about shaft member 148.

As discussed above, jet assembly 104 is positioned within recess 112 of motor assembly 102 when pump 100 is fully assembled. In that regard, jet assembly 104 is magnetically coupled to motor assembly 102 when jet assembly 104 is positioned within recess 112. Specially, the magnetic polar array 110 of motor assembly 102 and the magnetic polar array 150 of jet assembly magnetically couple together the motor assembly 102 and jet assembly 104.

Moreover, during operation of motor assembly 102, shaft member 108 is rotated such that the magnetic field generated by magnetic pole array 110 moves or fluctuates in accordance with the rotation of the magnetic pole array 110. This moving or fluctuating magnetic field moves and/or causes rotation of magnetic pole array 150 of impeller 130. Additionally, as discussed in greater detail below, rotation of impeller member 130 results in fluid being drawn towards impeller member 130 through inlet apertures 134 and such fluid to be propelled out of jet assembly 104 through outlet aperture 136.

Figure 7A:
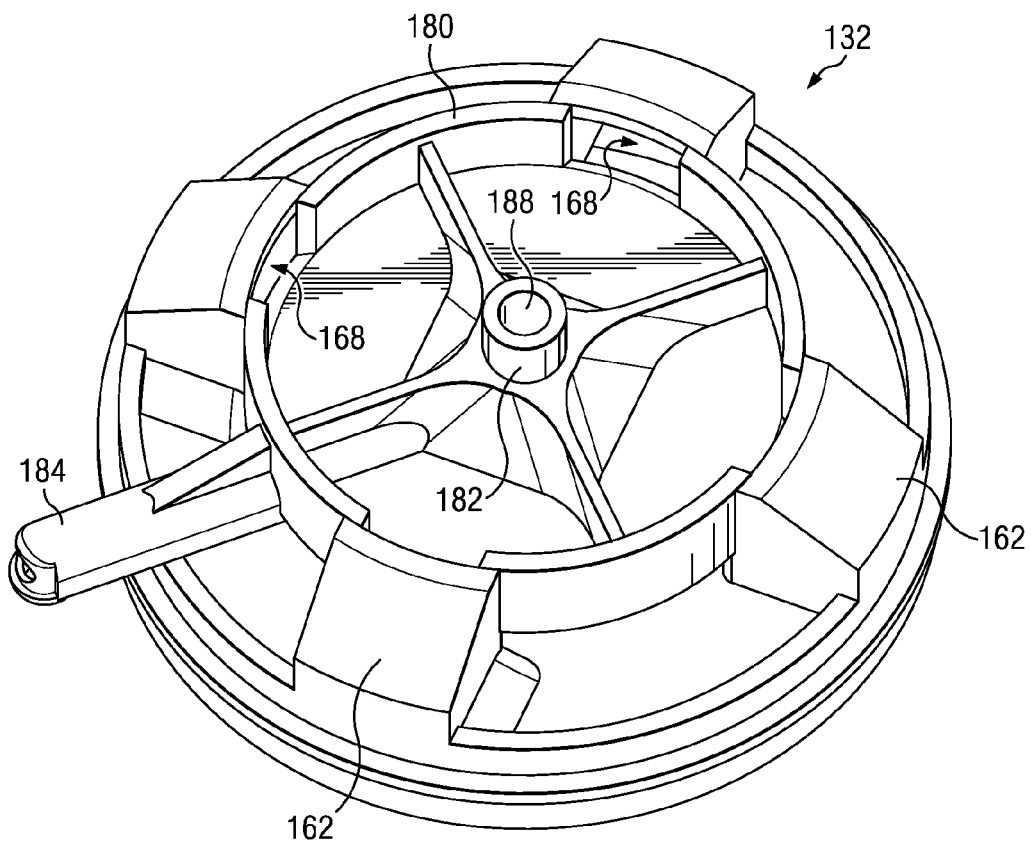
FIGS. 7A-7C illustrate perspective views of a fluid guider of the jet assembly of FIG. 6.
Figure 7B:
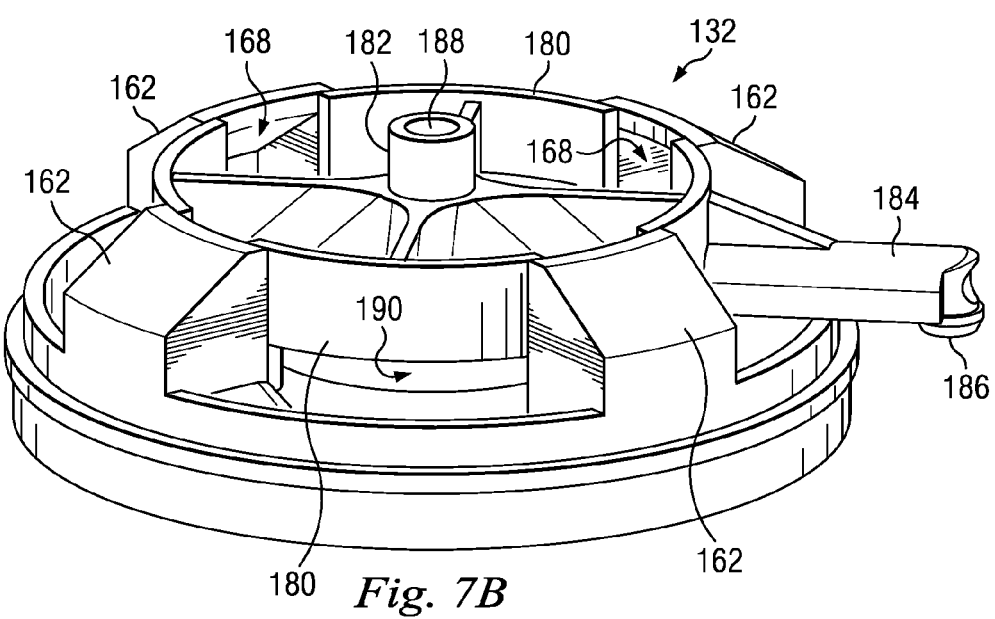
Figure 7C:
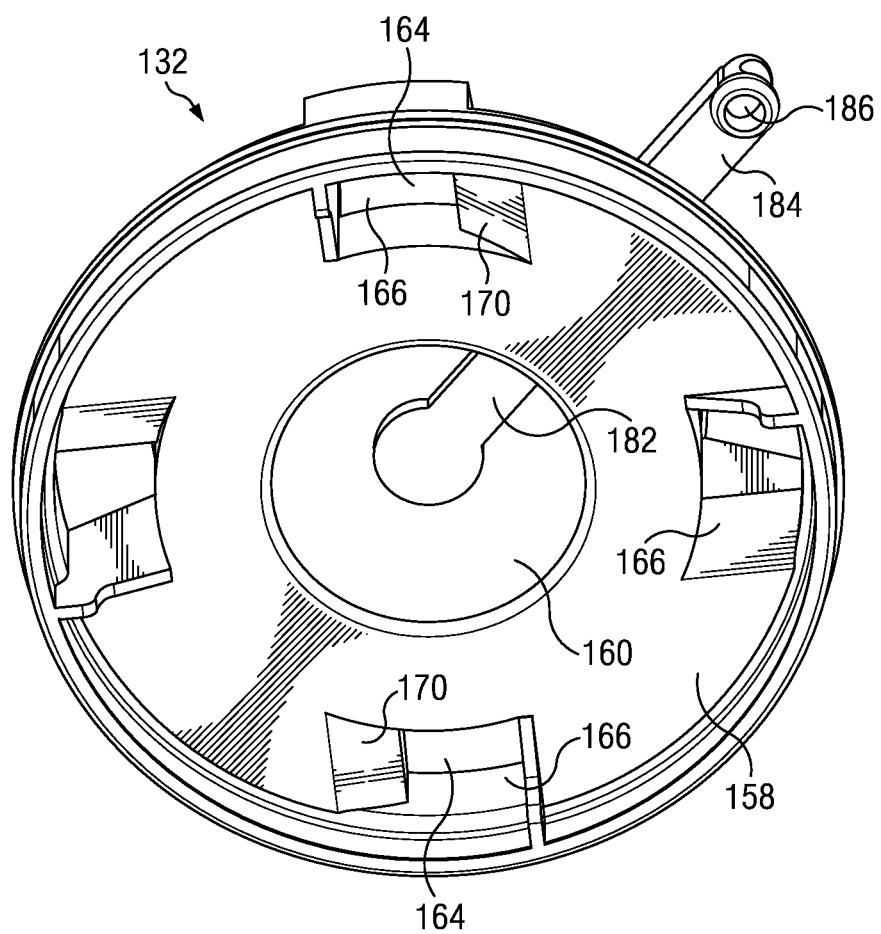
Figure 8A:
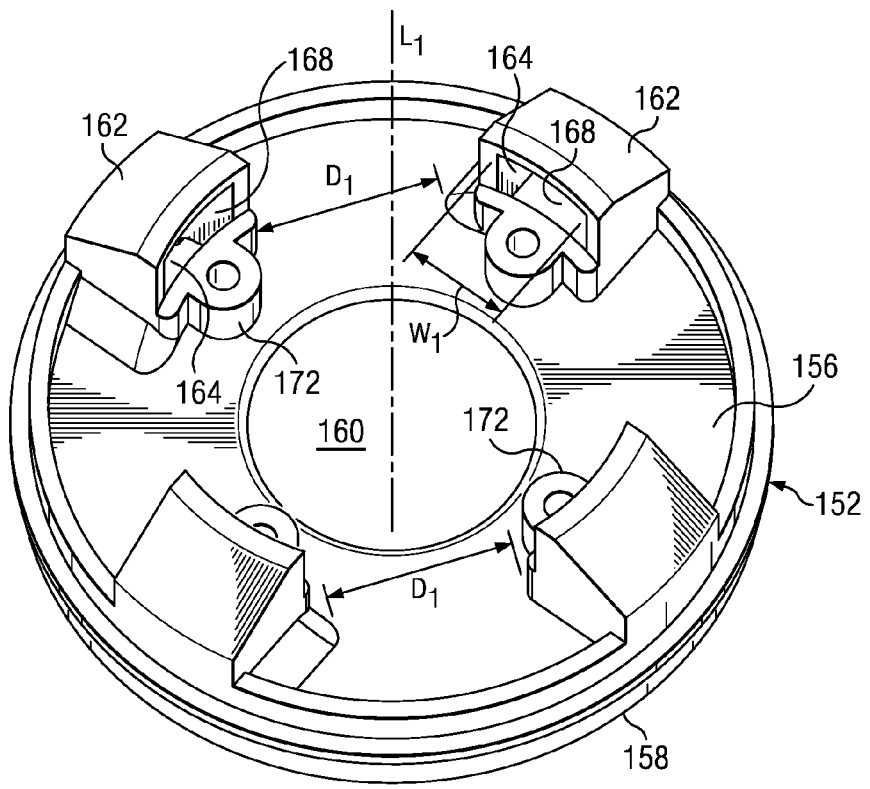
FIGS. 8A-8B illustrate perspective views of a lower component of the fluid guider of FIGS. 7A-7C.
Figure 8B:
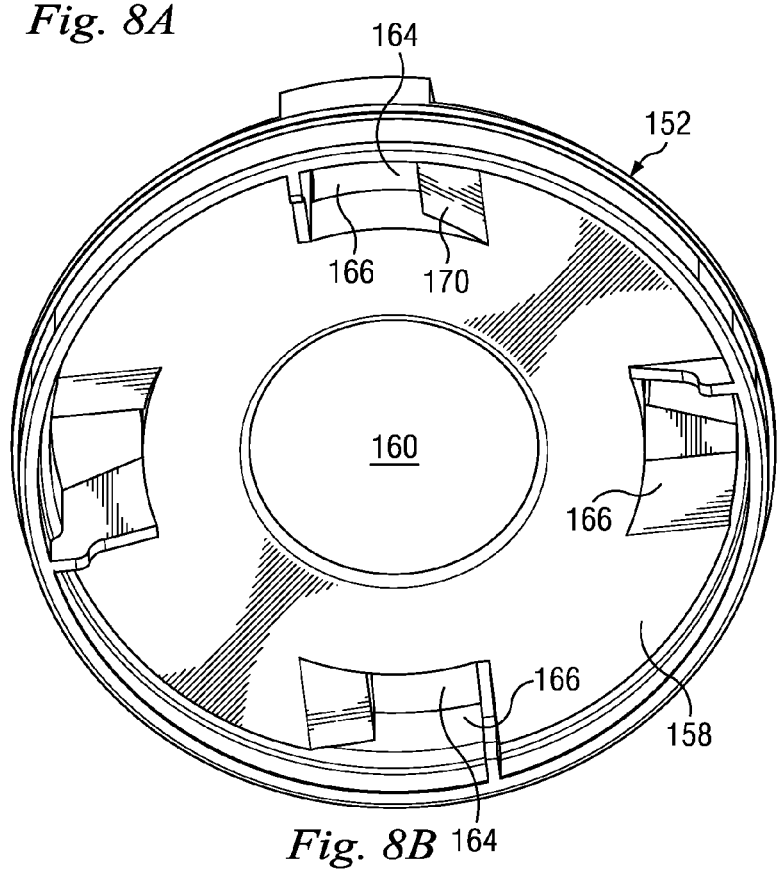

The jet assembly further includes fluid guider 132. FIGS. 7A-7C show fluid guider 132 in an assembled state and FIGS. 8A-9B show the fluid guider 132 in a disassembled state. Fluid guider 132 includes a lower component 152 and an upper component 154. As shown in FIGS. 8A and 8B, lower component 152 has an top surface 156 and an opposing bottom surface 158. Centrally positioned within top surface 156 is an aperture 160 that extends from the top surface through to the bottom surface 158.

Extending from top surface 156 along longitudinal axis $L_1$ are posts or pillars 162. As shown, lower component 152 includes four posts 162 equally distanced or spaced from each other a distance $D_1$ around the perimeter, or outer edge, of lower component 152. As shown in FIG. 8A, each post 162 is positioned such that it directly opposes and faces another post 162. Moreover, each post 162 has substantially the same width. However, in other embodiments there may be more than four posts or less than four posts associated with lower component 152. Moreover, in other embodiments posts 162 may be spaced unequal distances from each other and/or have varying widths.

Posts 162 each define a channel 164 extending through each post. Channel 164 extends from an inlet aperture 166 on bottom surface 158 to an outlet aperture 168 positioned above top surface 156. As shown in FIG. 8A, outlet apertures 168 of each post 162 have substantially the same width $W_1$. Moreover, each post 162 is positioned such that each post's outlet aperture 168 directly opposes and faces another post's outlet aperture 168. As such, when fluid is distributed out of each post's outlet aperture 168, the respective fluid streams from each post are directed toward the central portion of lower component 152. That is, the respective fluid streams from each post are expelled or outputted at an oblique angle with respect to longitudinal axis $L_1$.

In some embodiments, the respective fluid streams are directed toward the central portion of lower component 152 at a substantially transverse or perpendicular angle with respect to longitudinal axis $L_1$. In other words, the respective fluid streams from each post are expelled, directed, and/or outputted toward the central portion of lower component 152 substantially along the same plane. Therefore, the respective fluid streams from each post's outlet aperture can be substantially coplanar with respect to each other when leaving the post.

In other embodiments, it contemplated that the respective fluid streams from each post's outlet aperture are directed toward the central portion of lower component 152 at any oblique angle with respect to longitudinal axis $L_1$. In such embodiments, the respective fluid streams from each post are directed toward the central portion of lower component 152 along substantially different planes. Therefore, the respective fluid streams from each post's outlet aperture can be substantially non-coplanar with respect to each other when leaving the post. Regardless of the particular angle with respect to longitudinal axis $L_1$, as discussed in greater detail below, the respective fluid stream from each post are combined together to form a jet fluid stream that exits the jet assembly 104 through outlet aperture 136.

Additionally, bottom surface 158 has a portion 170 that is tapered or sloped that leads into channel 164 through inlet aperture 166. Furthermore, each post 162 includes an attachment feature 172 that is configured to couple the lower component 152 with the upper component 154. Here, the attachment features 172 include a recess designed to receive a protrusion to snap fit, press fit, or otherwise couple the upper component 154 to the lower component 152.

Figure 9A:
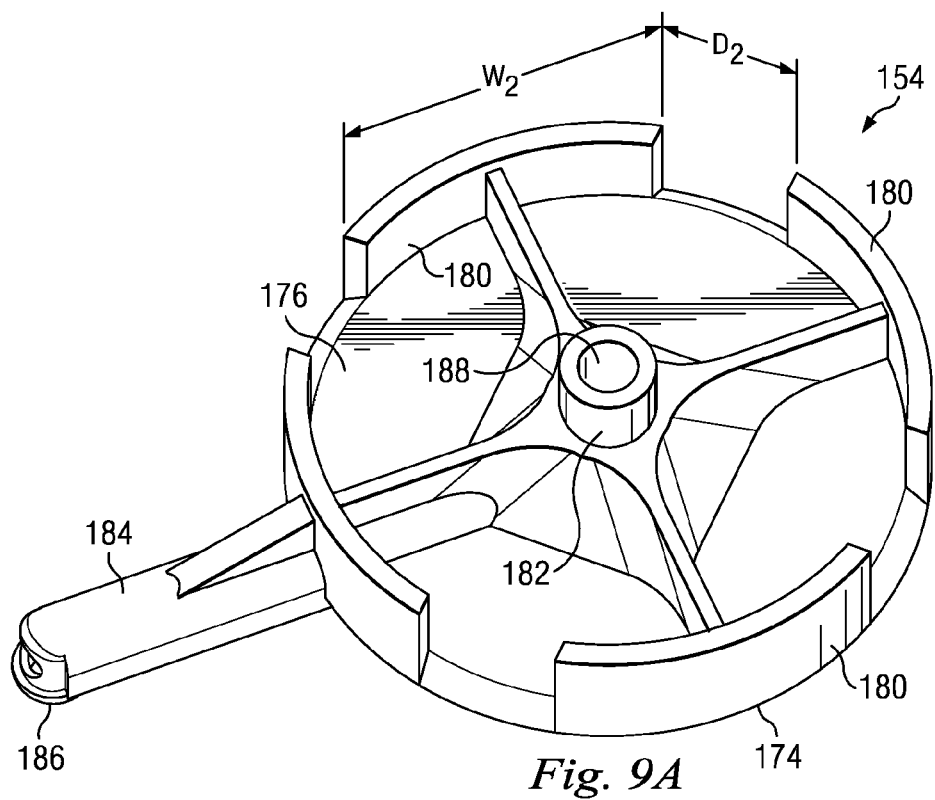
FIGS. 9A-9B illustrate perspective views of an upper component of the fluid guider of FIGS. 7A-7C.
Figure 9B:
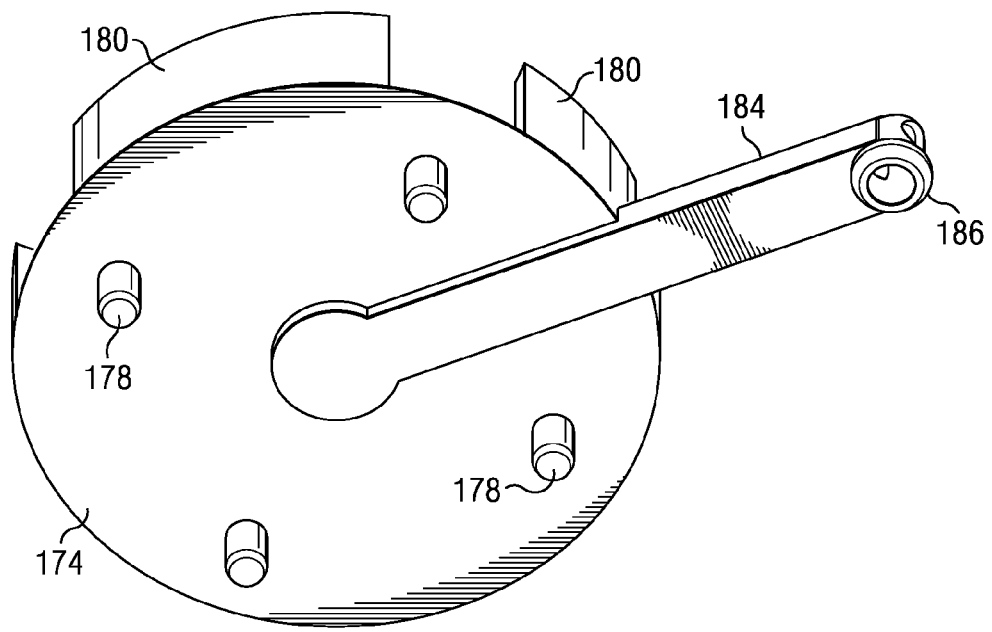

Referring to FIGS. 9A and 9B, upper component 154 includes a bottom surface 174 and a top surface 176. Extending from bottom surface 174 are protrusions 178. As discussed above, protrusions 178 are sized and shaped to interact with attachment features 172 of lower component 152 to thereby couple the lower component 152 and upper component 154 together. Moreover, as discussed in more detail below, the interaction of attachment features 172 with protrusions 178 acts as alignment guides that ensure that the upper component 154 and lower component 152 are properly aligned with respect to each other when assembled.

Extending from top surface 176 are wall members 180. As shown, upper component 154 includes four wall members 180 that are equally distanced or spaced from each other a distance $D_2$ around the perimeter, or outer edge, of upper component 154. Moreover, each wall member 180 has substantially the same width $W_2$. However, in other embodiments there may be more than four wall members or less than four wall members associated with upper component 154. Moreover, in other embodiments wall members 180 may be spaced unequal distances from each other and/or have varying widths.

Additionally extending from top surface 176 is air channel member 182, or a second fluid channel member. As shown, air channel 182 extends from a central portion of top surface 176. The central portion of top surface 176 is tapered and/or sloped towards air channel 182. Furthermore, air channel 182 extends through upper component 154 along the top surface 176 and bottom surface 174. Additionally, a portion 184 of air channel 182 extends through and beyond one of wall members 180.

Air channel 182 includes an inlet 186 and outlet 188. As shown in FIG. 1, air channel 182 is in communication with air channel 114. Specifically, the outlet 118 of air channel 114 is in communication with the inlet 186 of air channel 182. Additionally, as shown in FIGS. 1 and 2, outlet 186 of air channel 182 is in communication with outlet aperture 136. Moreover, outlet 186 is aligned such that outlet 186 is substantially centrally disposed within aperture 136. As will be described in greater detail below, air channel 182 in combination with air channel 114 of motor assembly 102 enables the jet assembly 104 to produce a jet stream of fluid that includes an air mixture.

As discussed above, the interaction of attachment features 172 with protrusions 178 acts as alignment guides that ensure that the upper component 154 and lower component 152 are properly aligned with respect to each other. As shown in FIG. 7B, this alignment is essential to the formation of channels 190, or pathways, positioned between each post 162. Specifically, upon coupling of lower component 152 and upper component 154, wall members 180 are aligned between each post 162. In that regard, the width $W_2$ of each wall member 180 is wider than the distance $D_1$ between each post 162. As a result, each wall member 180 positioned between a respective pair of posts blocks a portion of distance $D_1$ between the posts.

Furthermore, because attachment features 172 extend from upper surface 156 of the lower component 152, the attachment features 172 act as a riser or ledge that upper component 154 engages when coupled to lower component 152. Thus, attachment features 172 prevent the bottom surface 174 of the upper component 154 from contacting the top surface 156 of the lower component 152. Therefore, attachment features 172 ensure that the coupling of lower component 152 and upper component 154 does not disrupt and/or prevent channel 190 from communicating with aperture 160 of lower component 152. In other words, the vertical height of attachment features 172 extending from top surface 156 dictate the degree to which channel 190 is able to communicate with aperture 160 of the lower component.

The interaction of attachment features 172 with protrusions 178 further acts as alignment guides with respect to properly aligning outlet apertures 168 between wall members 180. As shown in FIGS. 7A and 7B, when lower component 152 and upper component 154 are coupled each post 162 is positioned between a pair of wall members 180. In that regard, the distance $D_2$ or the space between each wall member 180 is substantially similar to the width $W_1$ of each post's outlet aperture 168. As a result, each post's outlet aperture 168 is substantially unobstructed by wall members 180 and directly opposes and faces another post's outlet aperture 168.

As discussed above, when lower component 152 and upper component 154 are coupled together, fluid guider 132 includes channels 190, or pathways, positioned between each posts 162. In that regard, as shown in FIG. 1, wall members 180 are positioned against front cover 126 when the jet assembly 104 is fully assembled. As such, wall members 180 prevent and/or redirect fluids being received from inlet apertures 134 into channel 190. As a result, fluid is moved through channel 190 towards aperture 160.

Moreover, as shown in FIGS. 1 and 7C, fluid flowing through aperture 160 is in communication with cavity, basin, or chamber 192 formed by the coupling of back cover 124 with front cover 126 of the jet assembly 104. Additionally, inlet apertures 166 of posts 162 are in communication with cavity 192 such that fluid received within inlet apertures 166 traverses through each post's channel 164. As discussed above, each post 162 is positioned such that each post's outlet aperture 168 directly opposes and faces another post's outlet aperture 168. As such, when fluid is distributed out of each post's outlet aperture 168, the respective fluid stream from each post is directed toward outlet 188 of air channel 182.

In some embodiments, the respective fluid streams are directed toward outlet 188 at a substantially transverse or perpendicular angle with respect to longitudinal axis $L_1$. In other words, the respective fluid streams from each post are expelled, directed, and/or outputted outlet 188 substantially along the same plane. Therefore, the respective fluid streams from each post's outlet aperture can be substantially coplanar with respect to each other when leaving the post.

In other embodiments, the respective fluid streams from each post's outlet aperture are directed toward outlet 188 at any oblique angle with respect to longitudinal axis $L_1$. In such embodiments, the respective fluid streams from each post are directed toward outlet 188 along substantially different planes. Therefore, the respective fluid streams from each post's outlet aperture can be substantially non-coplanar with respect to each other when leaving the post. Regardless of the particular angle with respect to longitudinal axis $L_1$, as discussed in greater detail below, the respective fluid stream from each post are combined together to form a jet fluid stream that exits the jet assembly 104 through outlet aperture 136.

Figure 10:
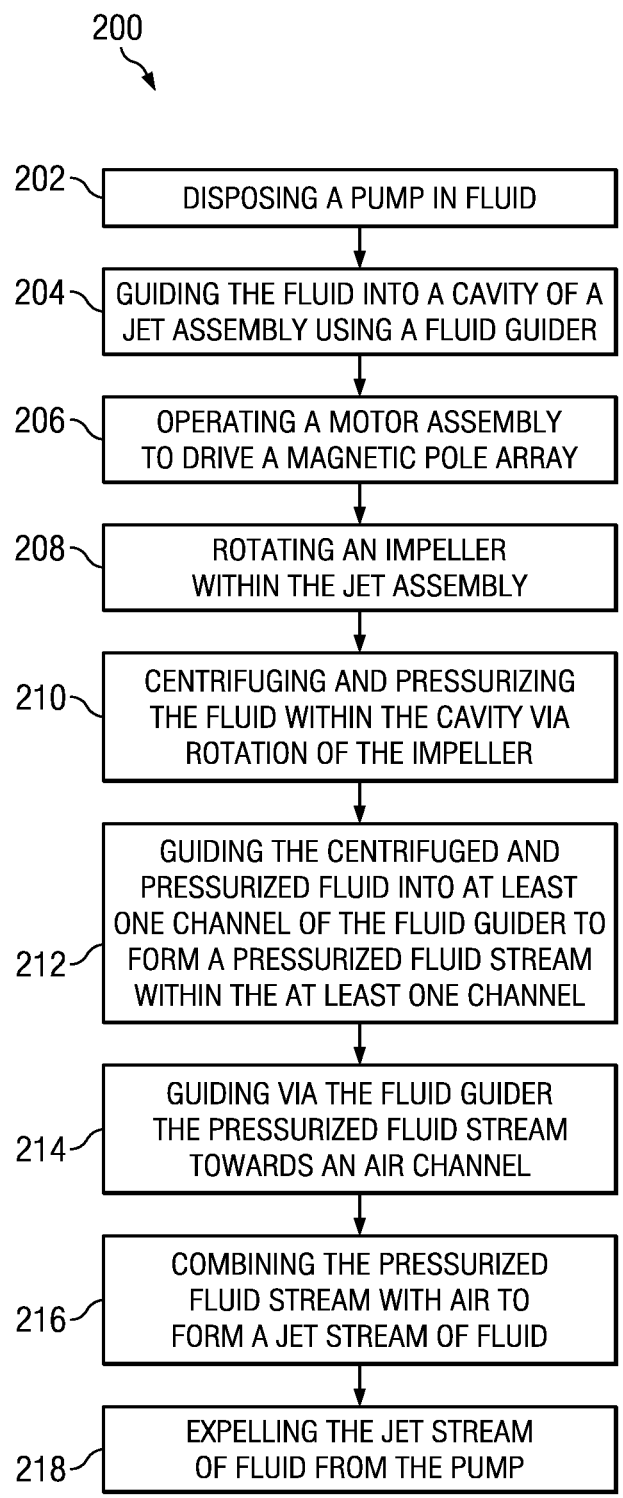
FIG. 10 illustrates a method of fluid distribution using the pump of FIG. 1.

FIG. 10 illustrates a method 200 of fluid distribution using pump 100. Method 200 begins at block 202 with disposing pump 100 in a fluid, such as water. Fluid enters into jet assembly 104 through inlet apertures 134 of front cover 126. As discussed above, inlet apertures 134 form a circular pattern around the front cover 126. Moreover, as discussed above, the circular pattern of inlet apertures 134 allows for a gradual gradient change for fluid intake into jet assembly 104.

At block 204, fluid guider 132 of jet assembly 104 guides the fluid into cavity 192 that houses impeller 130. In that regard, as shown in FIG. 1, wall members 180 of fluid guider 132 are positioned against front cover 126 when the jet assembly 104 is fully assembled. As such, wall members 180 prevent and/or redirect fluid being received from inlet apertures 134 into channels 190. As a result, fluid is moved through channels 190 into cavity 192 via communication with aperture 160 of fluid guider 132. The fluid entering cavity 192 from channels 190 can be considered a low pressure fluid with respect to the pressure of fluid expelled from the jet assembly 104.

At block 206, motor assembly 102 is operated in order to rotate or drive magnetic pole array 110. In that regard, shaft member 108 of motor assembly 102 is rotated such that the magnetic field generated by magnetic pole array 110 moves or fluctuates in accordance with the rotation of the magnetic pole array 110.

At block 208, in response to the movement and/or fluctuation of the magnetic field generated by magnetic pole array 110, impeller 130 rotates within jet assembly 104. As discussed above, impeller 130 contains a magnetic pole array 150 that causes the impeller to rotate about shaft member 148 in response to the movement and/or fluctuation of the magnetic field generated by magnetic pole array 110.

Rotation of impeller 130 causes fluid in cavity 192 to be centrifuged and pressurized at block 210. The centrifuged and pressurized fluid is guided and/or propelled towards inlet apertures 166 of posts 162. Additionally, because impeller 130 forces fluid out of cavity 192 and into channels 164 of posts 162, this draws additional fluid into cavity 192 from channels 190 of the guider assembly 132. The fluid exiting cavity 192 into channels 164 can be considered a high pressure fluid with respect to the pressure of fluid received into cavity 192 from channels 190.

At block 212, the centrifuged and pressurized fluid is guided into channels 164 of posts 162. Specifically, the centrifuged and pressurized fluid is received through inlet apertures 166 and into channels 164. In that regard, portion 170, that is tapered or sloped, of fluid guider 132 helps to guide or direct the centrifuged and pressurized fluid into channels 164. Moreover, the centrifuged and pressurized fluid within channels 164 represents respective pressurized fluid streams within each post 162.

At block 214, the respective pressurized fluid streams within each post 162 are guided toward air outlet 188 of air channel 182. As discussed above, each post 162 is positioned such that each post's outlet aperture 168 directly opposes and faces another post's outlet aperture 168. As such, when the pressurized fluid stream is distributed out of each post's outlet aperture 168, the respective pressurized fluid streams from each post are directed toward outlet 188 of air channel 182. That is, the pressurized fluid stream is directed toward outlet 188 at an oblique angle with respect to longitudinal axis $L_1$ of each post 162, jet assembly 104, and/or pump 100. As discussed above, it is contemplated that the pressurized fluid stream can be directed toward outlet 188 at any oblique angle with respect to a longitudinal axis of each post 162, jet assembly 104, and/or pump 100 as long as the pressurized fluid stream is directed at outlet 188.

At block 216, the pressurized fluid streams from each post 162 are combined together with air (i.e. a second fluid) from outlet 188 to form a jet fluid stream. As discussed above, each post 162 is positioned such that each post's outlet aperture 168 directly opposes and faces another post's outlet aperture 168. As such, when the pressurized fluid stream is distributed out of each post's outlet aperture 168, the respective pressurized fluid streams from each post are directed toward outlet 188 of air channel 182. Thus, the pressurized fluid streams from each post 162 intersect, converge, and/or combine with each other in and around outlet 188 of air channel 182.

Moreover, the pressurized fluid streams from each post pass across outlet 188 of the air channel 182. The flow of the pressurized fluid streams across outlet 188 encourages a flow of air from within air channel 182 to be mixed with the pressurized fluid streams. Specifically, the flow of the pressurized fluid streams across or over outlet 188 generates a suction force that causes air to flow into inlet 116 and through the air channels 114 and 182 and out outlet 188. Thus, this air flow is combined with the pressurized fluid streams to form a jet stream of fluid.

As a result, the jet stream of fluid is expelled, outputted, or propelled through the outlet aperture 136 of the front cover 126 of jet assembly 104 at block 218. As discussed above, outlet aperture 136 is centrally positioned on front cover 126. As such, the jet stream of fluid is expelled from the central position of front cover 126. In that regard, the jet stream of fluid flows substantially in the direction of the longitudinal axis $L_1$ of pump 100. Moreover, the air within the jet stream of fluid produces bubbles that rise to the surface of the fluid and creates an aesthetically pleasing effect.

However, in other embodiments the jet stream of fluid may flow substantially at an oblique angle with respect to the longitudinal axis of pump 100. For example, outlet aperture 136 can be configured to have an eyelet or directionally controlled port that dictates the axial direction for expelling the jet stream of fluid from jet assembly 104.

It should be noted, as discussed above, jet assembly 104 includes LED array 140. In that regard, energy harvester component 128 is configured to garner and utilize the magnetic waves produced from the rotation of magnetic pole array 110 through electromagnetic induction. Thus, during method 200 LED array 140 can be controlled by controller 142, as discussed above, to produce any color, pattern of color, intensity, sequencing of illumination desired, and/or any other parameter discussed above with respect to controller 142. The addition of LED array 140 provides a pleasing therapeutic affect in the fluid and/or jet stream of fluid.

Figure 11:
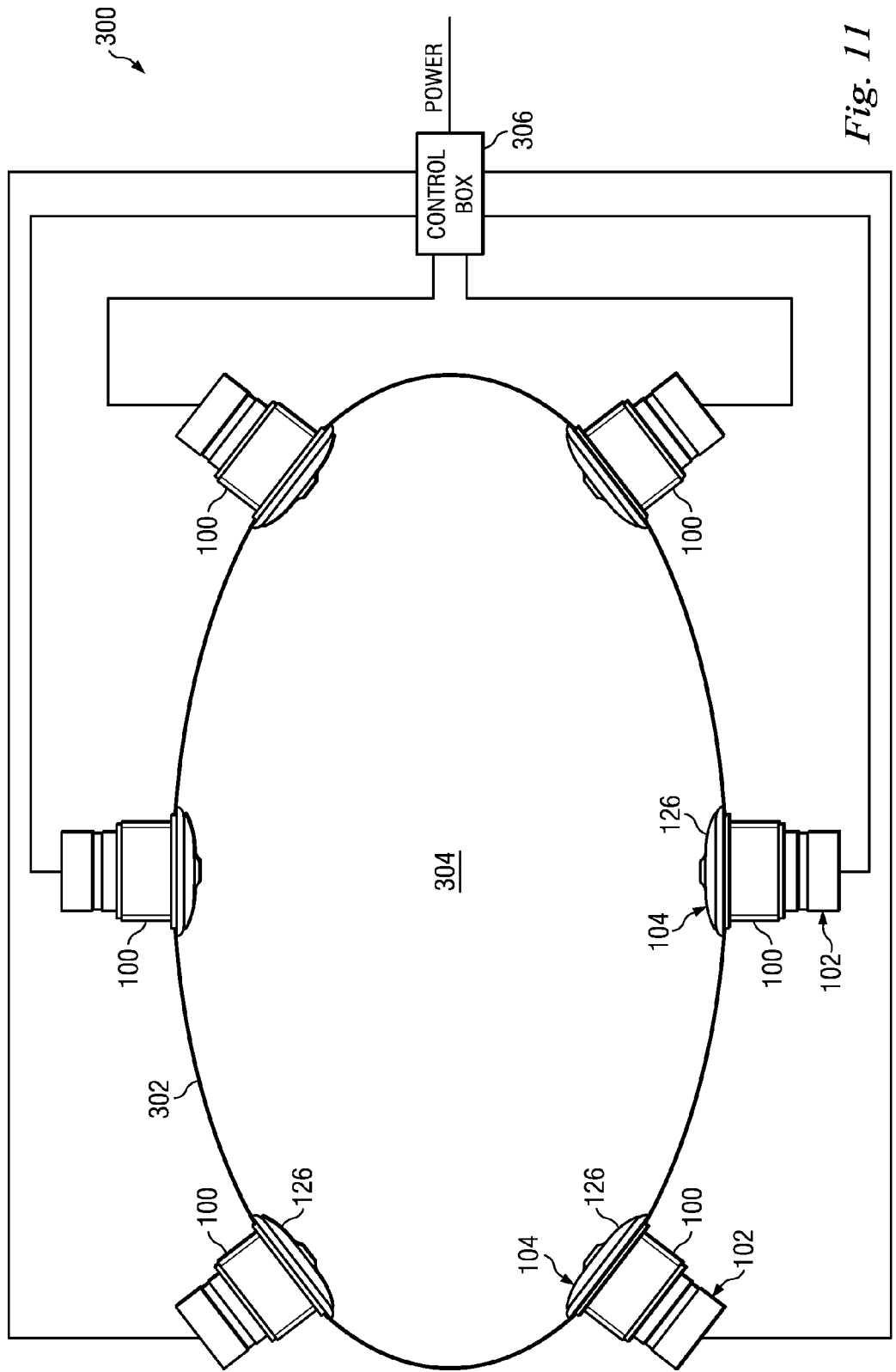
FIG. 11 illustrates a fluid control system using the pump of FIG. 1.

FIG. 11 illustrates a fluid control system 300 using a plurality of pumps 100. In that regard, each pump 100 is positioned within a wall of fluid container 302. Fluid container 302, for example, may be any spa device including, but not limited to, any device used for hydrotherapy, massage, stimulation, pedicure, bathing purposes, and the like. Here, for example, the interior of fluid container 302 is holding a fluid 304, such as water.

A hole or recess sized and shaped to receive each pump 100 may be formed in the wall of fluid container 302. For example, the hole or recess may be preformed within fluid container 302. Moreover, each pump 100 may be placed within a hole or recess which may have been drilled from the interior of the fluid container 302. As shown, each pump 100 is substantially flush with the wall of fluid container 302. Here, only front cover 126 of each pump 100 extends into the interior portion of fluid container 302.

It is understood that the number of pumps and the position of the pumps may vary depending on a particular design. The pumps 100 are coupled to a system controller or control box 306 for controlling the operation of the pumps by a user of the fluid control system 300. For example, the pumps 100 may be controlled independently of each other such that one or more of the pumps can be powered on/off, may be controlled according to a program that powers the pumps in various patterns or cycles, or may be controlled using a timer. The control box 306 may be hard wired to a power source or may be a plug-in type.

As discussed above, each pump 100 includes LED array 140 that produces lighting effects that illuminate fluid 304. In that regard, control box 306, can be used to control the controllers 142 within each pump 100. Thus, control box 306 can be used to control controllers 142 to produce any color, pattern of color, intensity, sequencing of illumination desired, and/or any other parameter discussed above with respect to controller 142. The addition of LED array 140 provides a pleasing therapeutic affect in the fluid 302.

Moreover, because LED array 140 is part of jet assembly 104 repairs and maintenance of the LEDs is easier than in a traditional spa device. Specifically, as discussed above, jet assembly 104 and motor assembly 102 are magnetically coupled together. Therefore, the two assemblies can easily be decoupled from each other without having to remove motor assembly 102 from fluid container 302. In that regard, jet assembly 104 is removed from fluid container 302 by simply pulling the jet assembly 104 towards the interior of fluid container 302. As a result, motor assembly 102 remains within fluid container 302 while repair and/or maintenance can be performed on jet assembly 104. Additionally, because jet assembly 104 has a built-in light source, such as LED array 140, there is no need to install a separate light source within fluid container 302.

While the preceding description shows and describes one or more embodiments, it will be understood by those skilled in the art that various changes in form and detail may be made therein without departing from the spirit and scope of the present disclosure. For example, various steps of the described methods may be executed in a different order or executed sequentially, combined, further divided, replaced with alternate steps, or removed entirely. In addition, various functions illustrated in the methods or described elsewhere in the disclosure may be combined to provide additional and/or alternate functions. Therefore, the claims should be interpreted in a broad manner, consistent with the present disclosure.

What is claimed is:

1. An apparatus comprising:
    a motor assembly having a motor and a magnetic array such that the motor is configured to drive the magnetic array;
    a jet assembly coupled to the motor assembly, the jet assembly including:
        an inlet aperture configured to receive a first fluid;
        an outlet aperture surrounded by the inlet aperture and centrally disposed about the jet assembly, the outlet aperture configured to output the first fluid;
        an impeller positioned within a cavity of the jet assembly and configured to rotate within the cavity when the magnetic array is driven such that rotation of the impeller causes the first fluid to flow into the inlet aperture and out the outlet aperture;
        a fluid guider in communication with the inlet and outlet apertures, the fluid guider comprising:
            at least one wall member defining a first channel configured to guide the first fluid from the inlet aperture into the cavity;
            at least one post defining a second channel extending through the post, the second channel configured to guide the first fluid from the cavity towards the outlet aperture and output the first fluid at an oblique angle with respect to a longitudinal axis of the post; and
            a second fluid channel member disposed within the outlet aperture and configured to provide a second fluid out the outlet aperture; and
    a light source configured to emit a light that illuminates the first fluid when the magnetic array is driven.

2. The apparatus of claim 1, wherein flow of the first fluid across an opening of the second fluid channel causes output of the second fluid such that a combination of the first and second fluids is outputted through the outlet aperture.

3. The apparatus of claim 1, wherein the at least one post includes a first post and a second post, the first post directly opposing the second post such that the first fluid outputted from the first post intersects with the first fluid outputted by the second post.

4. The apparatus of claim 1, wherein the at least one wall member includes a first wall member and a second wall member and the at least one post is disposed between the first and second wall members.

5. The apparatus of claim 4, wherein the first and second wall members are spaced apart a first distance and the least at least post has an outlet aperture having a width substantially equal to the first distance.

6. The apparatus of claim 1, wherein the jet assembly further comprises:
    a coil configured to capture magnetic waves produced from the magnetic array to provide energy to the light source;
    and
    a controller coupled to the coil and the light source and configured to control a parameter associated with the light source.

7. The apparatus of claim 6, wherein the light source is an array of light emitting diodes disposed about a perimeter of the jet assembly.

8. The apparatus of claim 7, wherein the parameter includes at least one of intensity, color, and illumination sequencing.

9. The apparatus of claim 1, wherein the fluid guider includes an upper component and a lower component, the upper component having the at least one wall member and the second fluid channel member, the lower component having the at least one post.

10. The apparatus of claim 9, wherein the at least one wall member includes a first wall member and a second wall member, and
    wherein the lower component has a first attachment feature and the upper component has a second attachment feature such that the first and second attachment features align and couple the upper and lower components together such that the at least one post is disposed between the first and second wall members.

11. The apparatus of claim 10, wherein the first attachment feature is one of a recess and a protrusion and the second attachment feature is the other of the recess and the protrusion.

12. The apparatus of claim 1, wherein the jet assembly further comprises a front cover and back cover that couple together to form the cavity,
wherein the inlet and outlet apertures are formed in the front cover, and
wherein the inlet aperture includes a plurality of apertures forming a circular pattern that surrounds the outlet aperture.

13. The apparatus of claim 1, wherein the motor assembly includes a sensor sensing a level of the first fluid around the apparatus such that if the sensor determines that the level of the first fluid around the apparatus is below a predetermined level then the sensors causes the motor assembly to stop driving the magnetic array.

14. A system comprising:
a motor assembly having a motor and a magnetic array such that the motor is configured to drive the magnetic array;
a jet assembly magnetically coupled to the motor assembly, the jet assembly including:
an inlet aperture configured to receive a first fluid;
an outlet aperture surrounded by the inlet aperture and centrally disposed about the jet assembly, the outlet aperture configured to output the first fluid;
an impeller positioned within a cavity of the jet assembly and configured to rotate within the cavity when the magnetic array is driven such that rotation of the impeller causes the first fluid to flow into the inlet aperture and out the outlet aperture;
a fluid guider in communication with the inlet and outlet apertures, the fluid guider comprising:
at least one wall member defining a first channel configured to guide the first fluid from the inlet aperture into the cavity;
at least one post defining a second channel extending through the post, the second channel configured to guide the first fluid from the cavity towards the outlet aperture and output the first fluid at an oblique angle with respect to a longitudinal axis of the post; and
a second fluid channel member disposed within the outlet aperture and configured to provide a second fluid out the outlet aperture; and
a light source configured to emit a light that illuminates the first fluid when the magnetic array is driven;
a fluid container having an interior portion for containing the first fluid, the interior portion having a first recess formed therein sized and shape to receive the motor assembly and the jet assembly; and
a system controller coupled to and operable to control the motor assembly and the jet assembly.

15. The system of claim 14, wherein flow of the first fluid across an opening of the second fluid channel causes output of the second fluid such that a combination of the first and second fluids is outputted through the outlet aperture.

16. The system of claim 14, wherein the second fluid channel member is formed from a portion of the motor assembly and the jet assembly and extends to an exterior portion that opposes the interior portion of the fluid container.

17. The system of claim 14, wherein the at least one post includes a first post that directly opposes a second post such that the first fluid outputted from the first post intersects with the first fluid outputted by the second post.

18. The system of claim 14 wherein the jet assembly further comprises a front cover and back cover that couple together to form the cavity, wherein the inlet and outlet apertures are formed in the front cover, and
wherein the inlet aperture includes a plurality of apertures forming a circular pattern that surrounds the outlet aperture, the outlet aperture and the circular pattern being substantially concentric.

19. The system of claim 14, wherein the first fluid is water and the second fluid is air.

20. The system of claim 14, wherein the motor assembly has a second recess sized and shaped to receive the jet assembly.

21. The system of claim 14, wherein the light source is an array of light emitting diodes disposed about a perimeter of the jet assembly, and
wherein the system controller is operable to control one of intensity, color, and illumination sequencing for the array of light emitting diodes.

22. The apparatus of claim 1, wherein the magnetic array includes a first magnetic pole that is coupled to the motor and configured to drive a second magnetic pole coupled to the impeller.

* * * * *